(12) United States Patent  (10) Patent No.: US 8,909,335 B2
Radzelovage  (45) Date of Patent: Dec. 9, 2014

(54) METHOD AND APPARATUS FOR APPLYING A RECTILINEAR BIPHASIC POWER WAVEFORM TO A LOAD

(71) Applicant: Zoll Medical Corporation, Chelmsford, MA (US)

(72) Inventor: James G. Radzelovage, Londonderry, NH (US)

(73) Assignee: Zoll Medical Corporation, Chelmsford, MA (US)

( * ) Notice: Subject to any disclaimer, the term of this patent is extended or adjusted under 35 U.S.C. 154(b) by 0 days.

(21) Appl. No.: 13/967,878

(22) Filed: Aug. 15, 2013

(65) Prior Publication Data

US 2014/0052204 A1 Feb. 20, 2014

Related U.S. Application Data

(60) Provisional application No. 61/691,137, filed on Aug. 20, 2012.

(51) Int. Cl.
*A61N 1/00* (2006.01)
*A61N 1/39* (2006.01)
*A61N 1/362* (2006.01)

(52) U.S. Cl.
CPC .............. *A61N 1/362* (2013.01); *A61N 1/3912* (2013.01)
USPC .......................................................... 607/5

(58) Field of Classification Search
USPC ............................................................ 607/5
See application file for complete search history.

(56) References Cited

U.S. PATENT DOCUMENTS

| | | |
|---|---|---|
| 5,690,693 A | 11/1997 | Wang et al. |
| 5,741,306 A | 4/1998 | Glegyak et al. |
| 5,852,358 A | 12/1998 | Ehsani |
| 6,148,233 A | 11/2000 | Owen et al. |
| 6,980,856 B2 * | 12/2005 | Sullivan et al. ................... 607/4 |
| 7,769,465 B2 | 8/2010 | Matos |
| 8,155,740 B2 | 4/2012 | Wanasek |
| 2001/0047140 A1 | 11/2001 | Freeman |
| 2007/0299473 A1 | 12/2007 | Matos |
| 2007/0299482 A1 * | 12/2007 | Littlewood et al. ............. 607/46 |
| 2010/0324612 A1 | 12/2010 | Matos |
| 2011/0288604 A1 | 11/2011 | Kaib et al. |
| 2012/0146797 A1 | 6/2012 | Oskin et al. |

OTHER PUBLICATIONS

International Search Report and Written Opinion of the International Searching Authority, or the Declaration for International Application No. PCT/US13/55110, mailed Jan. 17, 2014, 14 pages.

* cited by examiner

*Primary Examiner* — George Manuel
(74) *Attorney, Agent, or Firm* — Lando & Anastasi, LLP

(57) ABSTRACT

A system and method to deliver a therapeutic quantity of energy to a patient. The system includes a capacitor having a rated energy storage capacity substantially equal to the therapeutic quantity of energy, a boost converter coupled with the capacitor and constructed to release energy from the capacitor at a substantially constant current for a time interval, and an H-bridge circuit coupled with the boost converter and constructed to apply the substantially constant current in a biphasic voltage waveform to the patient. The method includes storing a quantity of energy substantially equal to the therapeutic quantity of energy in a capacitor, releasing the quantity of energy at a relatively constant current during a time interval using a boost converter coupled with the capacitor, and delivering a portion of the quantity energy in a direction to the patient using an H-bridge circuit coupled with the boost converter.

20 Claims, 11 Drawing Sheets

METHOD AND APPARATUS FOR APPLYING A RECTILINEAR BIPHASIC POWER WAVEFORM TO A LOAD

RELATED APPLICATIONS

This application claims priority under 35 U.S.C. §119(e) to U.S. Provisional Application Ser. No. 61/691,137, titled "METHOD AND APPARATUS FOR APPLYING A RECTILINEAR BIPHASIC POWER WAVEFORM TO A LOAD," filed on Aug. 20, 2012, which is hereby incorporated herein by reference in its entirety.

BACKGROUND

1. Field

Aspects of embodiments relate generally to methods and apparatus for applying a selected energy impulse to a load without exceeding a safe power level. More particularly, aspects of embodiments relate to applying electrical energy impulses to a patient for therapeutic medical purposes. Even more particularly, aspects of embodiments relate to such methods and apparatus as used in heart defibrillators and/or pacing devices.

2. Discussion of Related Art

Current defibrillator technology stores electrical energy on a capacitor, a passive energy storage element, preparatory to applying a timed, e.g., 10 msec, rectilinear, biphasic energy impulse of a desired magnitude to a patient. In a known defibrillator, energy is applied as a current from the capacitor through the patient in a first phase, i.e., a first direction, for the first 6 msec of the energy impulse, and then as a current also from the capacitor, but through the patient in an opposite phase to the first phase, i.e., in a second direction opposite to the first direction, for the remaining 4 msec of the energy impulse. In order to accommodate a wide range of patients and operating conditions, especially the voltage droop that occurs as energy is transferred out of the capacitor, the capacitor is charged to a higher level of energy than required to produce the desired energy delivery. The above-described, known defibrillator incorporates a resistor network into which excess energy is dissipated by diverting a portion of the current from being delivered to the patient when sensors detect that power levels may be dissipated in the patient that exceed safe power levels.

SUMMARY

According to aspects of an embodiment, a method of applying a rectilinear biphasic electric power waveform to deliver a therapeutic quantity of energy to treat a patient presenting an electrical load is provided. The method comprises storing a quantity of energy substantially equal to and without substantially exceeding the therapeutic quantity of energy on a capacitor, and releasing the stored energy during a first interval in a first direction through the load presented by the patient, in a controlled manner using a boost converter. The method may further comprise releasing the stored energy during a second interval in a second direction through the load presented by the patient. The method may yet further comprise substantially exhausting the stored energy over the first interval and the second interval combined without exceeding a predetermined maximum safe power level when the load presented by the patient is between approximately 25Ω and 200Ω. The method may even yet further comprise releasing a portion of the stored energy from the capacitor into an inductor; releasing the portion of the stored energy from the inductor into the load; and controlling the releasing of the portion of energy into the inductor and into the load in an alternating sequence so as to produce a substantially even flow of energy into the load. According to other aspects of the embodiment, the therapeutic quantity of energy and the first interval are selected to pace a patient whose heart requires pacing impulses. According to yet other aspects of the embodiment, the therapeutic quantity of energy and the first interval are selected to defibrillate a patient whose heart is in fibrillation.

According to aspects of another embodiment, a system for applying a rectilinear biphasic electric power waveform to deliver a therapeutic quantity of energy to treat a patient presenting an electrical load is provided. The system comprises a capacitor having a rated energy storage capacity substantially equal to the therapeutic quantity of energy, a boost converter constructed and arranged to meter energy out of the capacitor as a substantially constant current while a voltage across the capacitor droops due to decreasing energy stored on the capacitor, and an H-bridge circuit constructed and arranged to apply the current to the patient in the rectilinear biphasic electric power waveform. The system may further comprise a controller that controls for a 10 msec combined first and second interval, and a 6 msec first interval.

According to aspects of an embodiment, a system to deliver a therapeutic quantity of energy to a patient load is provided. The system comprises capacitor having a rated energy storage capacity substantially equal to the therapeutic quantity of energy, a boost converter coupled with the capacitor and constructed to release energy from the capacitor at a substantially constant current for a time interval, and an H-bridge circuit coupled with the boost converter and constructed to apply the substantially constant current in a biphasic voltage waveform to the patient load.

According to an embodiment, the boost converter comprises an inductor coupled with the capacitor, a current sensing network, and a solid-state switch coupled between the inductor and the current sensing network. The boost converter may further comprise a controller circuit coupled with the solid state switch and the current sensing network and constructed to cycle the solid state switch. According to other aspects of the embodiment, the current sensing network is constructed to receive a current profile and compare the current profile with a received current from the solid state switch.

According to an embodiment, the H-bridge circuit comprises a plurality of switches, each of the plurality of switches including a circuit constructed to control the switch and to receive a phase profile having a first phase and a second phase. According to other aspects of the embodiment, the H-bridge circuit may further comprise an inverter coupled with at least two of the plurality of switches to invert the phase profile. At least two switches of the plurality of switches may be configured to be in an open state during the first phase and in a closed state during the second phase.

According to an embodiment, the boost converter circuit is further constructed to compensate for voltage droop on the capacitor and variation in the patient load over the time interval. According to an embodiment, the therapeutic quantity of energy and the time interval are selected to defibrillate a patient whose heart is in fibrillation. According to an embodiment, the therapeutic quantity of energy and the time interval are selected to pace a patient whose heart requires pacing impulses.

According to aspects of an embodiment, a method of delivering a therapeutic quantity of energy to a patient load is provided. The method comprises storing a quantity of energy substantially equal to the therapeutic quantity of energy in a capacitor, releasing the quantity of energy at a relatively constant current during a time interval using a boost converter coupled with the capacitor, and delivering a first portion of the quantity energy in a first direction to the patient load using an H-bridge circuit coupled with the boost converter. According to an embodiment, the method further comprises delivering a second portion of the quantity of energy in a second direction to the patient load using the H-bridge circuit.

According to an embodiment, releasing the quantity of the stored energy includes transferring energy to an inductor coupled with the capacitor, and sensing the amount of current through a solid state switch coupled between the inductor and a current sensing network. According to an embodiment, releasing the quantity of energy includes cycling the solid state switch using a controller circuit coupled with the solid state switch and the current sensing network. According to an embodiment, releasing the quantity of energy further includes receiving a current profile and comparing the current profile with the amount of current through the solid state switch using the current sensing network.

According to an embodiment, the H-bridge circuit comprises a plurality of switches and wherein delivering a first portion of the quantity energy in a first direction and a second portion of the quantity of energy in a second direction includes controlling the plurality of switches. According to an embodiment, controlling the plurality of switches includes receiving a phase profile having a first phase and a second phase. According to other aspects of an embodiment, controlling the plurality of switches further includes changing a state of at least 4 switches of the plurality of switches in response to receiving a change in the phase profile from the first phase to the second phase.

According to an embodiment, releasing the quantity of energy includes compensating for voltage droop on the capacitor and variation in patient load impedance over the time interval. According to an embodiment, the method further comprises determining the therapeutic quantity of energy and the time interval to defibrillate a patient whose heart is in fibrillation. According to an embodiment, the method further comprises determining the therapeutic quantity of energy and the time interval to pace a patient whose heart requires pacing impulses.

According to aspects of yet another embodiment, a method of maintaining a target power flow from a charge storage device to a patient load while voltage on the charge storage device droops, comprises inserting a boost converter between the charge storage device and the patient load to maintain power flow. The method may further comprise controlling a current delivered by the boost converter so as to compensate for voltage droop on the charge storage device and so as to compensate for variation in patient load impedance over time.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
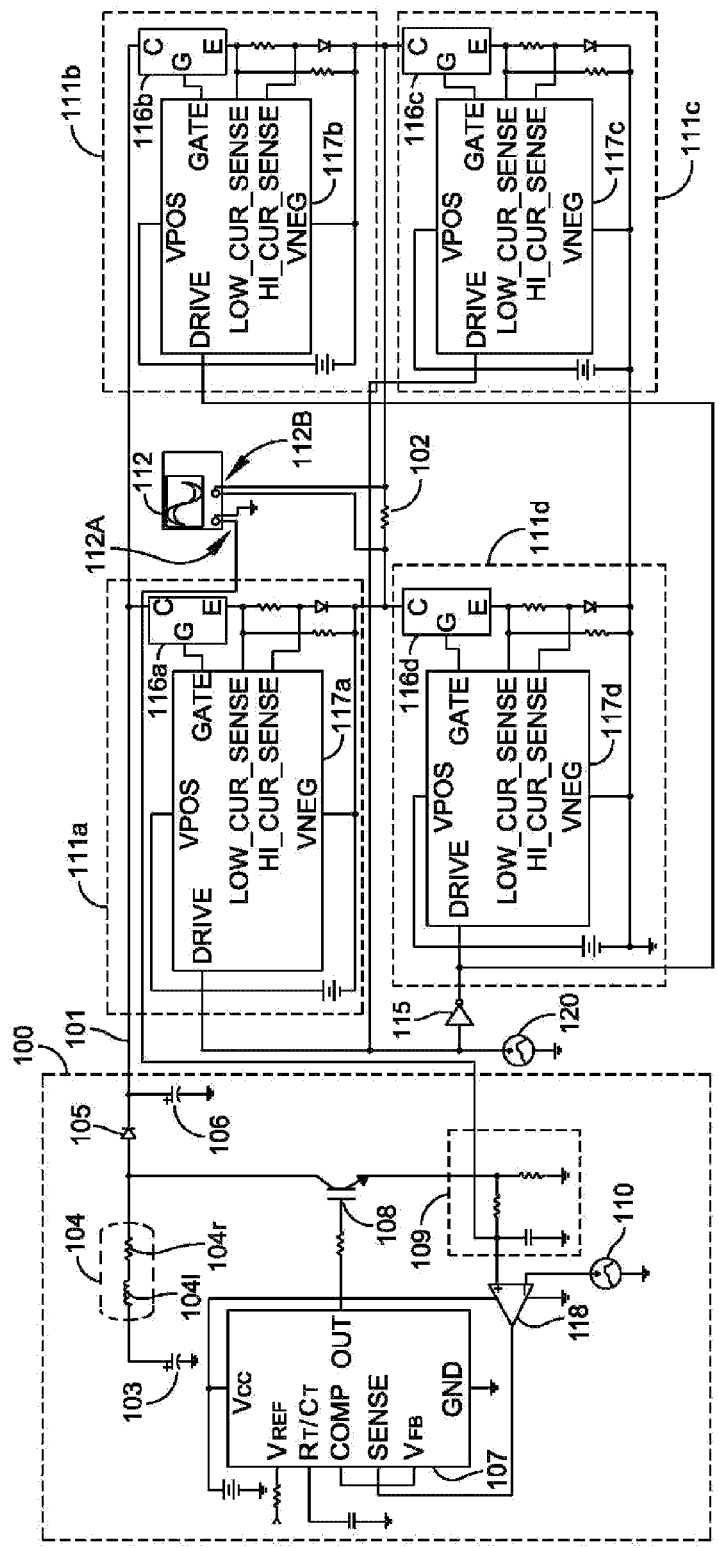
FIG. 1 is a schematic drawing of a circuit for delivering a rectilinear biphasic electric power waveform to deliver a therapeutic quantity of energy to treat a patient presenting an electrical load.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

As noted in the BACKGROUND section, defibrillators are devices that deliver a desired quantity of energy to a patient without exceeding a safe power level. Energy is simply power delivered to a load over a period of time:

$$Pt = E;$$

or $$P = \frac{E}{t};$$

where P represents power in Watts, E represents energy in Joules, and t represents the period of time in seconds over which the energy is delivered. When electrical energy is dissipated in a simple resistive load, that is, one which resists a flow of electrical current when a voltage is applied, power may be expressed in terms of the voltage applied to the load, voltage being a measure of electrical pressure across the load, and current through the load, current being a measure of movement of charge through the load. Electrical power is:

$$P = VI;$$

or $$P = I^2 R;$$

or $$P = \frac{V^2}{R};$$

where V represents voltage in Volts, I represents current in Amperes, and R represents the resistance of the load in Ohms.

Defibrillators store the desired quantity of electrical energy on a capacitor, as a charge. Storing a charge on a capacitor causes a voltage to appear across the terminals of the capacitor. When a user of a defibrillator applies a therapeutic shock to a patient, the electrical energy stored on the capacitor is released through the patient, whose body provides substantially a simple resistive load in which the energy is dissipated. As the capacitor supplies energy to the load, the charge on the capacitor decreases, and so the voltage appearing across the capacitor also decreases. As voltage decreases, or sags, the current driven through the load also decreases. Applying any of the definitions of electrical power given above, it is observed that the power, $P_O$, delivered by the capacitor at the beginning of a therapeutic shock of a defined magnitude, $E_O$, is greater than the power, $P_N$, delivered by the capacitor at the end of the therapeutic shock because the voltage on the capacitor sags as the charge on the capacitor is depleted by supplying current to the patient.

Conventionally, in order to accommodate the voltage sag, while delivering a constant, desired maximum power level until the desired energy impulse has been delivered, the size of the capacitor is selected to provide the desired energy impulse to a worst-case load at the end of the energy impulse. For these purposes, a worst-case load may be considered to be one at a lower end of an expected resistance range, since such a load will require a larger current to maintain a constant power level during the energy impulse. Such a design requires a capacitor that, when charged to a level that yields the desired energy impulse, dissipates in the patient a power level in excess of that desired during the initial portion of the energy impulse. As previously explained, during times of excess power delivery, the excess energy is simply dissipated into resistors so as to reduce to desired maximum levels the power delivered to the load, i.e., the patient, which both wastes power and necessitates the use of a capacitor whose rated energy storage capacity is greater than the maximum energy delivery requirement, since energy is dumped into the dissipation resistors and not recovered or otherwise put to therapeutic use.

Using a capacitor whose rated energy storage capacity is greater than the maximum energy delivery requirement is disadvantageous from several perspectives. For a given capacitor technology, greater storage capacity requires greater size and/or weight. A physically larger capacitor is undesirable, particularly for use in portable equipment, because equipment must be built larger and is more difficult to transport. Size and weight factors can prove prohibitive for equipment meant to be worn by, transported with, or carried by, a patient who themselves may not be fully ambulatory. Moreover, energy that is wasted, yet must be stored on the capacitor as described above, adds to the charging time and the performance characteristics required of the charging circuit which places the energy on the capacitor.

For example, in the conventional defibrillator described in the BACKGROUND section in which excess energy is dissipated into dissipation resistors, a capacitor having a minimum required energy rating of approximately 381 Joules is used. Under favorable conditions for maximum energy shock (i.e., a 200 Joule setting into a patient presenting an impedance of 161Ω), approximately 69% of the capacitor's minimum required energy rating is delivered to the patient. For higher impedance patients, energy utilization drops off slightly to 67% for a patient presenting an impedance of 175Ω, and to 63% for a patient presenting an impedance of 200Ω. The drop off in energy utilization is more severe for lower impedance patients (e.g., 37% for a patient presenting a 25Ω impedance, and 21% for a patient presenting a 15Ω impedance), primarily due to energy dissipated in the dissipation resistors. One of the physically smallest capacitors validated for use in such a conventional defibrillator weighs approximately 10 oz (283.5 grams) and has a volume of approximately 20 in$^3$ (327.7 cm$^3$).

According to aspects of embodiments, a boost converter is employed to control and regulate the delivery of a constant current, resulting in a constant power dissipation level during the delivery of a desired energy impulse. In brief summary, a boost converter transfers energy in very short bursts compared to the time for delivering the total desired energy impulse, first from the capacitor to an inductor, which stores the energy as a substantially constant current, and then from the inductor to the patient. Because the current delivered to the patient by the inductor is substantially constant due to the intrinsic electrical characteristics of inductors which tend to resist a change to current through them, a constant, maximum desired power level is dissipated in the patient, in accordance with the definitions of electrical power given above. A boost converter circuit of a defibrillator incorporating aspects of embodiments is now described in greater detail.

First, the basic boost converter circuit is described in connection with FIG. 1. The boost converter circuit, 100, provides a substantially constant current at its output node, 101, when that node is connected to a load, 102. The circuit, 100, includes a storage capacitor, 103, in which the energy for the desired impulse is held until a discharge into the patient load is triggered; an inductor, 104, connected to receive a current from the storage capacitor, 103, when the discharge is triggered; a diode, 105, to protect against a reversal of the current discharge; and, optionally a smoothing capacitor, 106; as well as control elements enumerated below. A charge circuit, such as a battery or other DC power source (not shown) is coupled to the storage capacitor 103, for example via relays, to provide energy to the storage capacitor 103. A terminal of the storage capacitor 103 is electrically coupled to a first terminal of the inductor 104, which in FIG. 1 is modeled as an inductor 1041 coupled in series with a resistor 104r. The second terminal of the inductor 104 is electrically coupled to the anode of the diode 105, with the cathode of the diode 105 being electrically coupled to a first terminal of the optional smoothing capacitor 106 and to the output node 101.

According to the capacitor energy equation, $E=\frac{1}{2}CV^2$, an exemplary capacitor, 103, of 270 μF, as shown in FIG. 1, charged to about 1218 V would store 200 Joules for the exemplary therapeutic shock. To deliver 200 Joules over a 10 msec impulse requires delivering a substantially constant, instantaneous power of 20 kW to the load, 102. If the load, 102, is 25Ω, then the power equation, $P=I^2R$, calls for a current of 28 A, while a load, 102, of 200Ω calls for a current of 10 A. Inductor, 104, is of a size to prevent substantial current droop while delivering a desired power level to the patient load, 102. A 1 mH inductor, 104, as shown in FIG. 1, produces the desired result, as illustrated below in FIGS. 2-6. In accordance with one embodiment, the inductor 104 may be an unsaturable 1 mH Litz wire air-core coil dimensioned to optimize self inductance.

While 100% utilization of the capacitor energy storage capability is the theoretical goal, practical circuit elements, which have real losses associated with them, achieve somewhat lower utilization rates, per the Table I, below. The simulations presented in FIGS. 2-6, and discussed below, assume capacitor, 103, has a capacitance of 270 μF, and an initial stored energy of 305 Joules.

TABLE I

| Patient Impedance | Therapeutic Shock Energy | 10 msec Continuous Power | Initial Energy Usage |
|---|---|---|---|
| 25 Ω | 249 Joules | 24.9 kW | 81% |
| 50 Ω | 255 Joules | 25.5 kW | 83% |
| 100 Ω | 236 Joules | 23.6 kW | 77% |
| 150 Ω | 221 Joules | 22.1 kW | 72% |
| 200 Ω | 210 Joules | 21.0 kW | 69% |

By comparison to a conventional defibrillator using a storage capacitor having a minimum energy rating of 381 Joules, embodiments of the present invention permit the use of a storage capacitor having an approximately 20% lower minimum energy rating (e.g., 305 Joules) while providing a similar amount of energy to the patient. As a result, the size and weight of the storage capacitor 103 used with embodiments of the present invention may be reduced by approximately 20% relative to storage capacitors used in a conventional defibrillator. Further efficiencies of size and cost are provided by eliminating the need for dissipation resistors and their associated shunting devices used in conventional defibrillators, as well as any of the thermal management features needed to dissipate the heat generated therefrom.

A specialized controller circuit, 107, modeled for convenience as a UC3842 current mode PWM controller, has a control output connected to a control input of a high-voltage and high-current, solid-state switch, 108 that is coupled between the second terminal of the inductor 104 and a current sensing network 109. The solid state switch 108 may be an IGBT as shown in FIG. 1, or another type of a high-voltage and high current solid state switch, such as a thyristor. It should be appreciated that embodiments of the present invention are not limited to the use of a particular type of PWM controller or to a particular type of high-current solid state switch, as other types of controller circuits, and other types of high-current switches may alternatively be used. Current drawn through the switch 108 is measured by the current sensing network, 109; compared to a desired current profile, 110; and, the result is provided as an input to the controller circuit, 107. Since, as explained above, current is directly related by a square law to instantaneous power, controlling for a desired current also controls for the desired instantaneous power level.

The load presented by the patient, 102, is connected to the output node, 101, through an H-bridge structure which causes current to flow through the patient in a desired direction at a desired time. The H-bridge includes four H-bridge switches 111, with each H-bridge switch 111a, 111b, 111c, 111d including a respective switching transistor 116a, 116b, 116c, 116d and a respective control circuit 117a, 117b, 117c, 117d associated with each. The switching transistors can be insulated-gate bipolar transistors (IGBTs), metal-oxide semiconductor field-effect transistors (MOSFETs), silicon-controlled rectifiers (SCRs) or such other high-current switching devices as may be available. In the exemplary, illustrative embodiment, for modeling purposes only, an oscilloscope, 112, having a channel A input, 112A, and a channel B input, 112B, has been included. Channel A, 112A, monitors the current impulses passed through the switch, 108, and channel B, 112B, monitors the voltage across the patient load, 102. The traces produced by channels A and B, 112A and 112B, are shown in FIG. 2, which is next referred to in an explanation of the operation of the circuit of FIG. 1.

Figure 2:
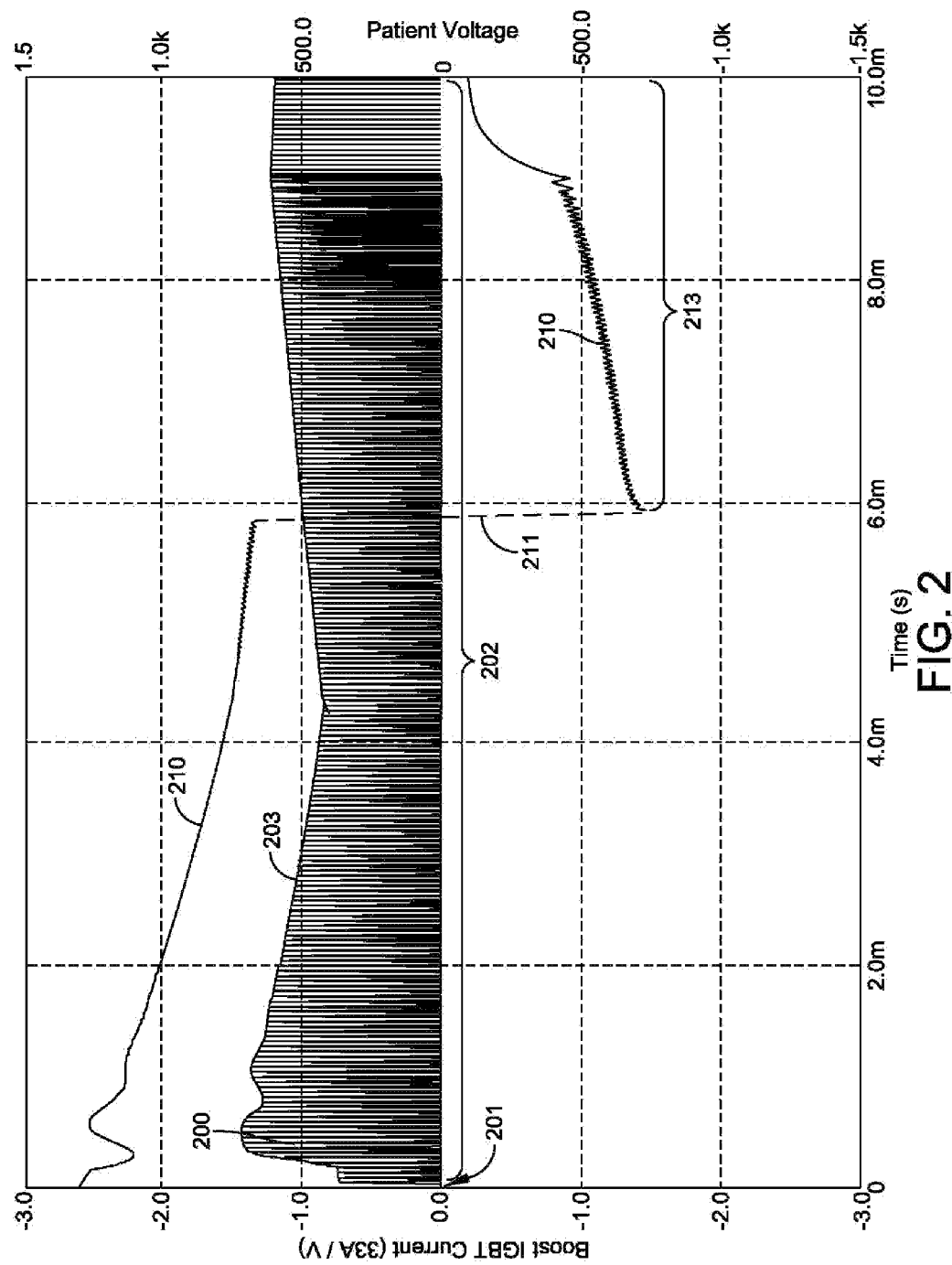
FIG. 2 is a graph of electrical waveforms produced by the circuit of FIG. 1 over a period of time with a patient load of 25Ω.

The circuit of FIG. 1 operates as follows to provide a 200-Joule defibrillation shock to a patient load, 102, of 25Ω, as illustrated in FIG. 2. The storage capacitor, 103, is first charged up with about 200 Joules of electrical energy, by a charging circuit (not shown). There are small, parasitic losses due to parasitic resistances throughout the circuits which deliver the charge to the patient, including parasitic resistances in the inductor, 104r, and elsewhere. If the parasitic resistances are negligible, then no more than about 200 Joules need be stored on the capacitor; however, if the parasitic resistances are non-negligible, then the storage capacitor, 103, should hold a small excess above the desired 200 Joules of electrical energy, the excess being sufficient to just account for the energy dissipated in the parasitic resistances under worst-case conditions. It should be appreciated that other shock energies (i.e., other than 200 Joules) may be provided, as known to those skilled in the art.

According to one embodiment, operation begins with the solid-state switch, 108, open, and each of the H-bridge switches, 111a-d, open. When a therapeutic shock is triggered, a pair of the H-bridge switches, e.g., 111a and 111c, is closed, initiating current through the patient load 102. Current then builds up in the inductor, 104. As shown in FIG. 2, indicated by line, 200, current through switch, 108, is zero during this initial period, 201. Next, during period, 202, the controller circuit, 107, begins cycling switch, 108, on and off, thereby allowing current through switch, 108. When the switch, 108, is closed and the controller circuit, 107, detects that the desired current or higher is flowing through the switch, 108, it provides a control signal to the solid-state switch, 108, to again open the switch, 108, allowing current through the inductor, 104, to the patient load, 102. At regular intervals, the controller, 107, closes the switch, 108, and checks for the current to build up to the desired level, at which point the control signal again opens the switch, 108.

During each cycle, during period, 202, when the controller circuit, 107, determines from the output of the current sensing network, 109, that the correct current level has been reached or exceeded, a control signal is applied to the solid-state switch, 108, to open the switch, allowing current through the inductor, 104, and the patient load, 102, from the energy stored on storage capacitor, 103. As current is initiated through the patient, a voltage, indicated in FIG. 2 by line 210, appears across the patient that causes the current in the inductor, 104, to begin to decay, and so the controller circuit, 107, again closes solid-state switch, 108, to begin the cycle again by building up the current stored in the inductor. By repeating the forgoing cycle many times during the therapeutic shock, energy stored on the storage capacitor, 103, is metered out to the patient without ever exceeding the maximum allowable power dissipation level in the patient. According to some embodiments, it has been found that the desired waveform to be applied to the patient reverses polarity after an interval. Accordingly, the H-bridge switches are controlled by a desired phase profile, 120, to open the closed pair of switches, 111a and 111c, and close the open pair of switches, 111b and 111d, at about 6 msec into the therapeutic shock cycle, reversing the polarity of the applied shock, 211. It should be noted that switches 111a and 111c are opened prior to closing switches 111b and 111d to avoid short-circuiting the H-bridge structure. The magnitude of the current applied to the patient load, 102, (and the resulting voltage across the patient load, 102) does not substantially change during the polarity reversal, 211 and 213.

As shown in FIGS. 3, 4, 5, and 6, the operation is similar for patients presenting resistance values of 50Ω, 100Ω, 150Ω, and 200Ω. The variation in the load, 102, results in different damping characteristics for the therapeutic shock waveforms, i.e., the overall shape of the waveform, and also results in different patient voltages, such that the 200 Joule impulse is applied as desired. In each of FIGS. 3, 4, 5, and 6, reference numerals indicating corresponding elements to elements of FIG. 2 correspond, except for the hundreds place, which corresponds to the FIG. number. For example, FIG. 2, line 200, corresponds to FIG. 3, line 300, but for a different patient load, 102.

Figure 3:
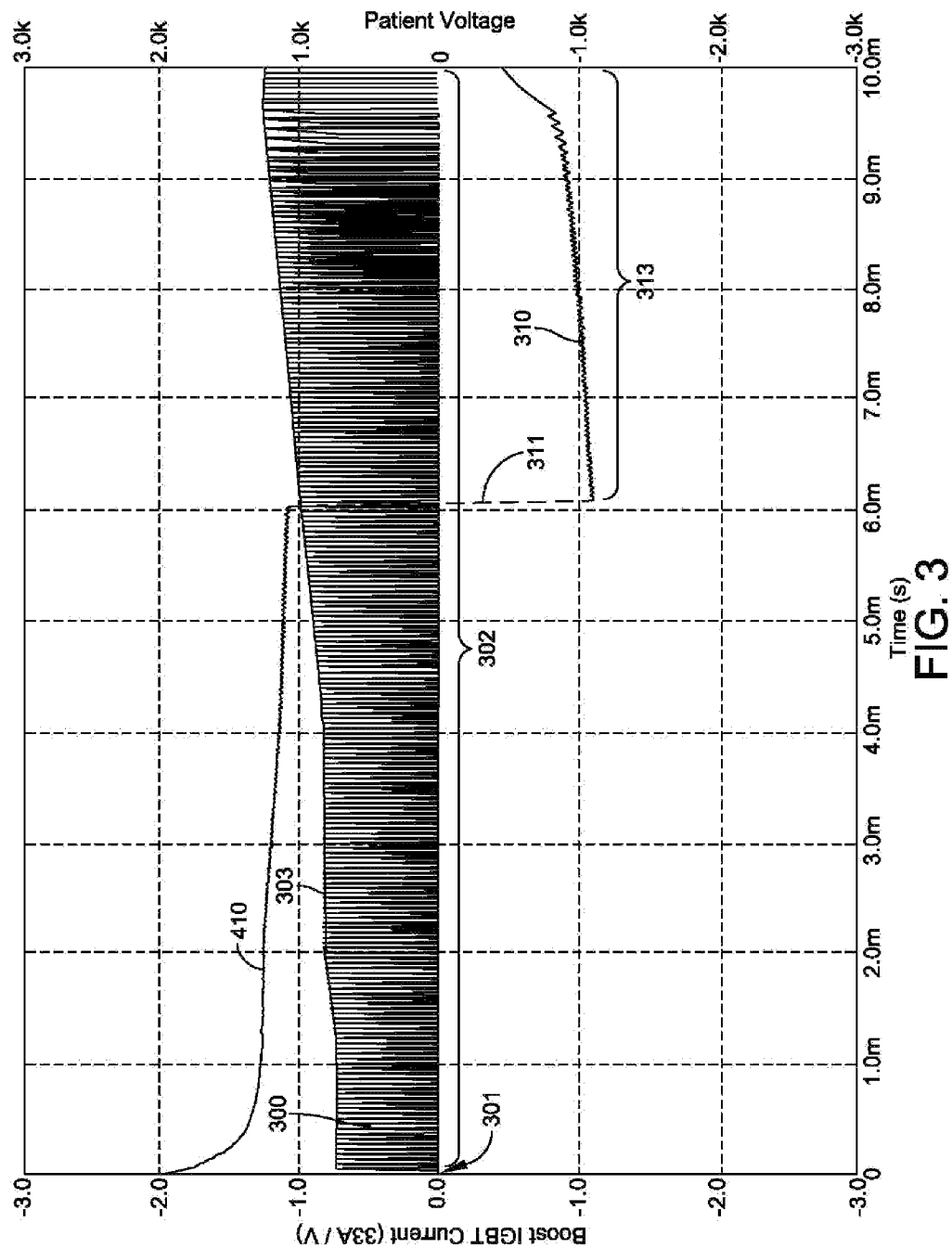
FIG. 3 is a graph of electrical waveforms produced by the circuit of FIG. 1 over a period of time with a patient load of 50Ω.
Figure 4:
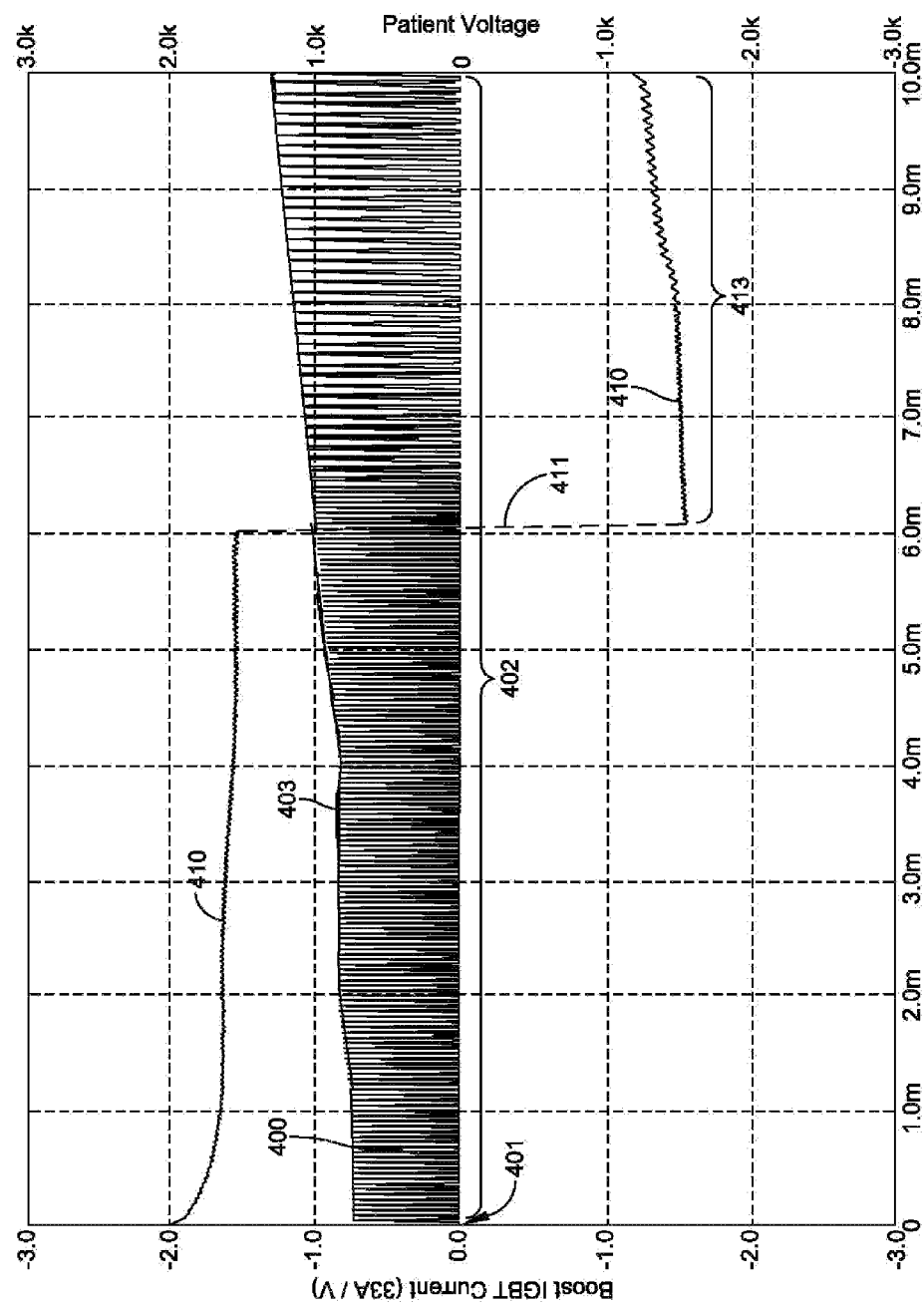
FIG. 4 is a graph of electrical waveforms produced by the circuit of FIG. 1 over a period of time with a patient load of 100Ω.
Figure 5:
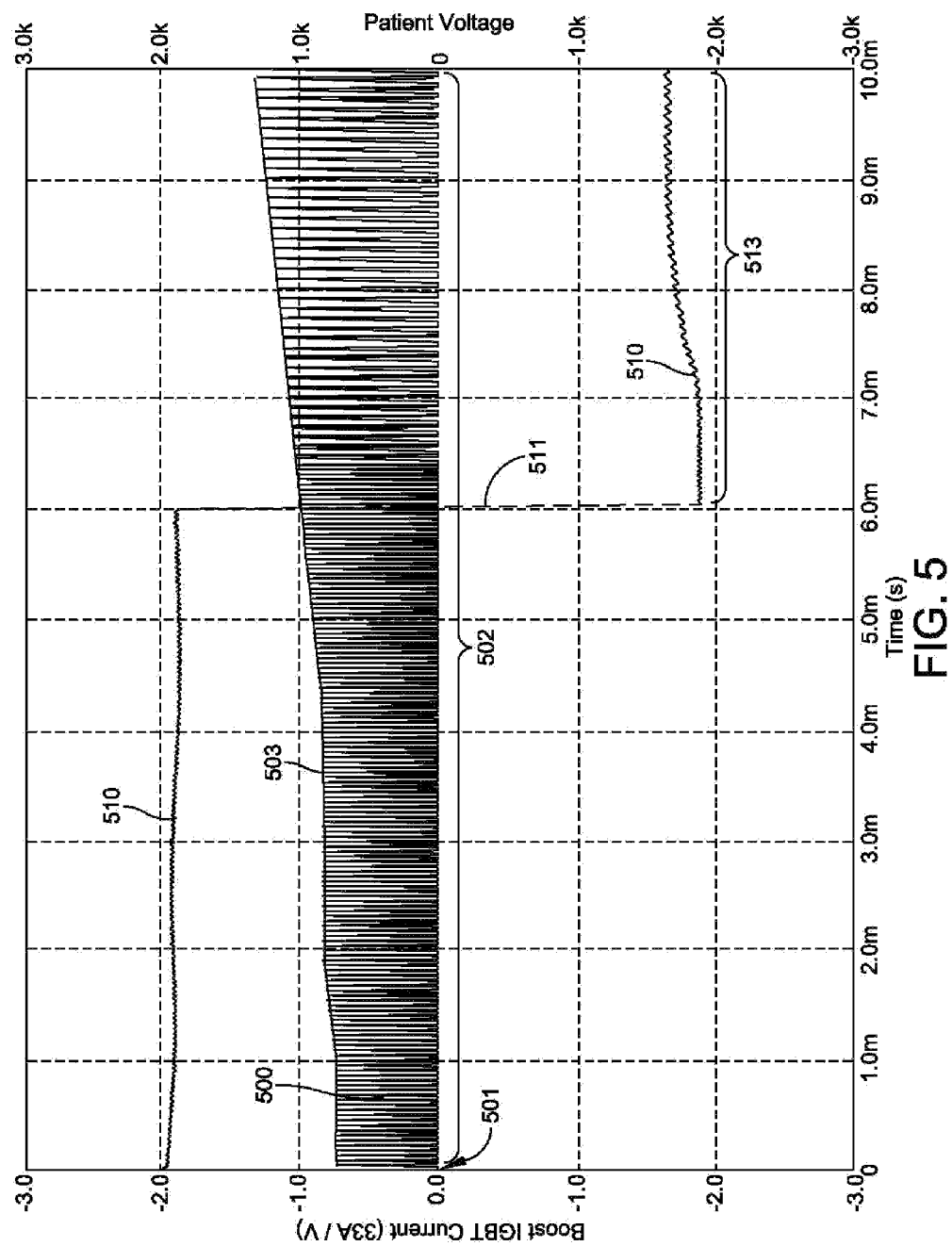
FIG. 5 is a graph of electrical waveforms produced by the circuit of FIG. 1 over a period of time with a patient load of 150Ω.
Figure 6:
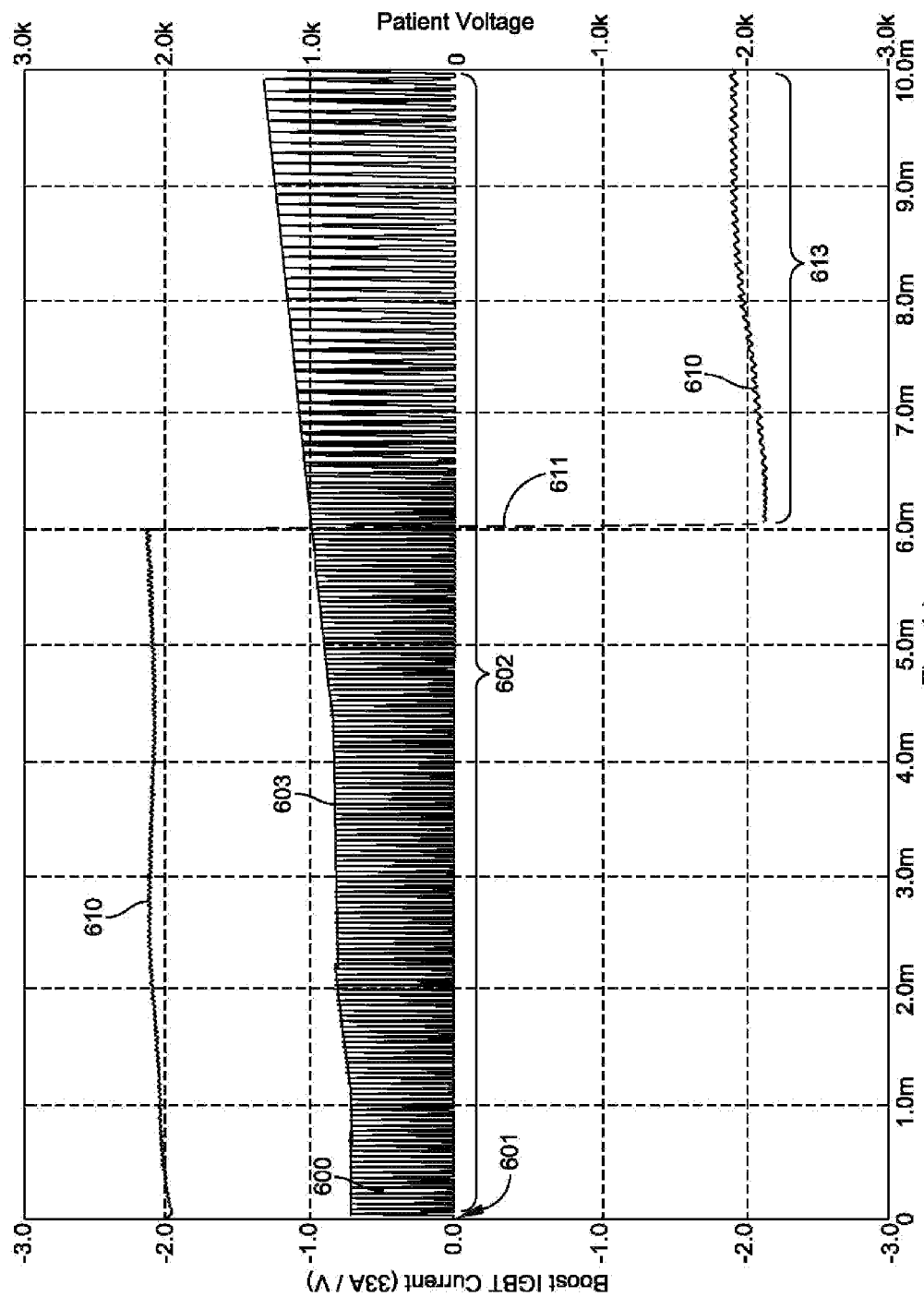
FIG. 6 is a graph of electrical waveforms produced by the circuit of FIG. 1 over a period of time with a patient load of 200Ω.

As shown in FIG. 2, for a patient load, 102, of 25Ω, the absolute value of patient voltage 210 varies between a peak of about 1.5 kV and 500 V. For a patient load, 102, of 50Ω, the absolute value of patient voltage 310 has a much flatter shape, as shown in FIG. 3. It hits a peak of about 2 kV but remains for most of the impulse at about 1.2 kV, finally tapering down to just under 1.0 kV. As shown in FIG. 4, for a patient load, 102, of 100Ω, the absolute value of patient voltage 410 has an even flatter shape. It also hits a peak of about 2 kV but remains for most of the impulse at about 1.5 kV, finally tapering down to about 1.2 kV. For a patient load, 102, of 150Ω, the absolute value of patient voltage 510 has a quite flat shape, as shown in FIG. 5. It hits a peak of about 2 kV but remains for nearly the entire impulse at about 1.8 kV. For a patient load, 102, of 200Ω, the absolute value of patient voltage 610 has a quite flat shape. It hits a peak of about 2 kV but remains for nearly the entire impulse at about 1.8 kV, as shown in FIG. 6.

In practical systems, the preference is to deliver substantially constant energy to the patient during a period of time. Thus, if a 200 Joule therapeutic shock is desired to be delivered in a 10 msec period, the controller circuit, 107, is designed or programmed to obtain a current level in the inductor, 104, that delivers 20 J/msec. The controller circuit, 107, in connection with the current sensing network, 109, the desired current profile, 110, and the solid state switch, 108, forms a feedback loop that controls and maintains the 20 J/msec level, or such other level or waveform as desired. Except for parasitic losses, explained below, the storage capacitor, 103, need only have a rated energy storage capacity of 200 Joules, since no excess energy is dumped and it is desired to leave no residual energy in the storage capacitor, 103, after the therapeutic shock has completed.

FIGS. 7A-F illustrate the manner in which the boost converter circuit 100 of FIG. 1 may be used to control the shape and/or phase of the defibrillating waveform applied to the patient. As described previously with respect to FIG. 1, current drawn through the switch 108 is measured by the current sensing network 109, compared to a desired current profile 110, and provided as an input to the controller circuit 107. In the circuit illustrated in FIG. 1, this comparison is performed by an operational amplifier 118 configured as a comparator. By controlling the shape and amplitude of the desired current profile 110, a waveform of a desired amplitude and desired shape may be delivered to the patient load 102.

Figure 7A:
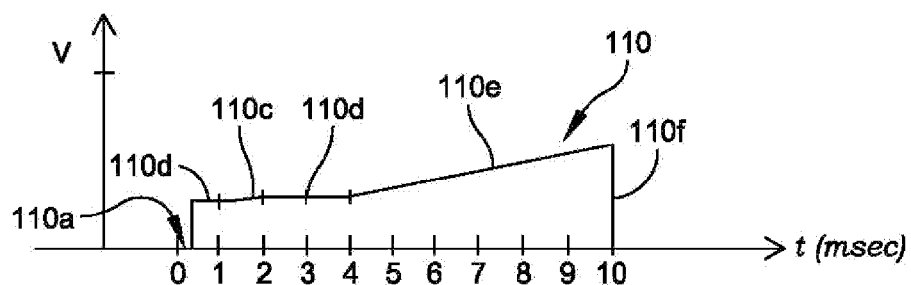
FIGS. 7A-F illustrate various current profiles and phase profiles that may be used with the circuit of FIG. 1 to deliver a variety of different defibrillating waveforms to the body of a patient.

For example, as shown in FIG. 7A, a current profile 110 having a step impulse that corresponds to a current level of approximately 22 A and that gradually increases to a level corresponding to approximately 40 A may be used to provide the current and voltage waveforms depicted in FIGS. 3-6. The current profile 110 is approximately 10 msec in duration and includes an initial period or region 110a where the current is zero (corresponding to periods 301, 401, 501, and 601 in FIGS. 3-6), followed by a step impulse (region 110b) corresponding to approximately 22 A. At approximately 1 msec, the current profile 110 linearly increases (region 110c) to a value corresponding to approximately 24 A. The current profile 110 remains at a level corresponding to about 24 A for about 2 msec (region 110d), where it then linearly increases (region 110e) to a level corresponding to approximately 40 A, after which the current profile returns to a zero current level (region 110f) at approximately 10 msec. The overall shape of the current profile 110 used to generate the current and voltage waveforms depicted in FIGS. 3-6 is shown in each respective figure by the respective envelope or profile 303, 403, 503, and 603 of the current through the switch 108. Differences in the voltage waveforms 310, 410, 510, and 610 applied to the patient in FIGS. 3-6 are primarily due to differences in the patient load 102. The overall shape of the current profile 110 used to generate the current and voltage waveforms depicted in FIG. 2 is shown in FIG. 2 by the envelope 203 of the current 200 through the switch 108.

Figure 7B:
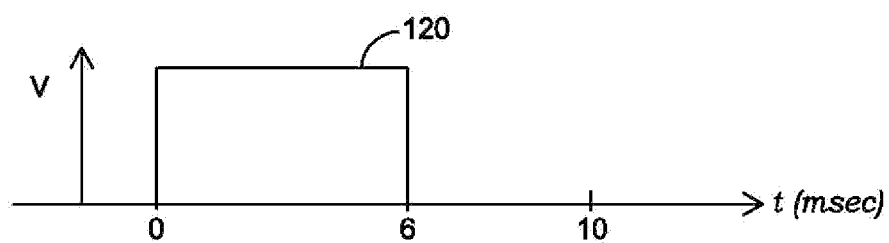

The phase of the defibrillating waveform that is applied to the patient may be controlled by the desired phase profile 120 provided to each of the H-bridge switches 111. For example, FIG. 7B illustrates a desired phase profile 120 that may be used to control the phase of the waveforms depicted in FIGS. 2-6. As shown, the phase profile 120 initially assumes a high state at time zero (or before) followed by a change to a low state at 6 msec. In the circuit depicted in FIG. 1, each of H-bridge switches 111a and 111c receives the phase profile 120, while each of H-bridge switches 111b and 111d receives an inverted version of the phase profile 120. The high state of the phase profile 120 operates to fully close each of H-bridge switches 111a and 111c during the initial 6 msec, and to maintain each of switches 111b and 111d in a fully open position. At approximately 6 msec, the level of the phase profile 120 changes, thereby fully opening H-bridge switches 111a and 111c, and fully closing switches 111b and 111d, thereby reversing the polarity of the delivered voltage waveform as shown in each of FIGS. 2-6. The presence of the inverter 115 serves to not only invert the phase profile 120, but to delay the signal provided to each of H-bridge switches 111b and 111d to help ensure that these switches are not closed until after switches 111a and 111c have opened. If necessary, additional delays could be provided. Where the switching transistors 116a, 116b, 116c, and 116d used in each of the H-bridge switches 111a, 111b, 111c, 111d are capable of operating in a linear mode, the high state and the low state of the phase profile 120 should be such that the switching transistors are either fully conducting (on) or fully non-conducting (off) to avoid thermal destruction.

Figure 7C:
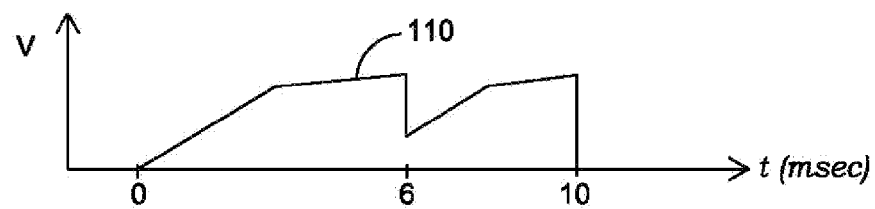
Figure 7D:
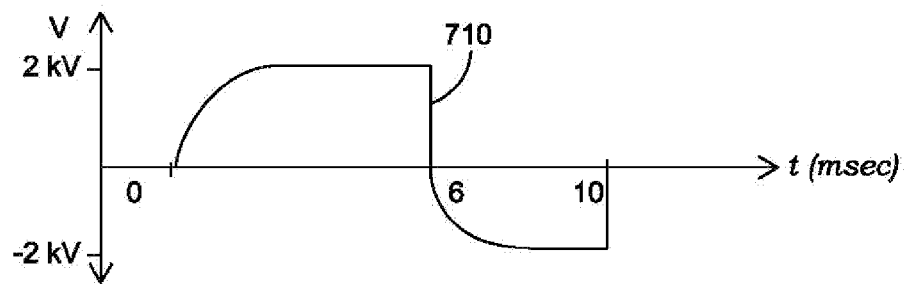

FIG. 7C illustrates an alternative desired current profile 110 that may be used with the boost converter circuit 100 of FIG. 1 to generate a biphasic voltage waveform that increases asymptotically from a zero value to a desired voltage level (e.g., to approximately 2 kV in amplitude for a 200Ω patient) over the initial portion of each phase. When combined with a phase profile 110 similar to that illustrated in FIG. 7B, the boost converter circuit 100 may provide a defibrillating voltage 710 to the body of the patient similar to that shown in FIG. 7D. As shown in FIG. 7D, the biphasic voltage waveform 710 is approximately 10 msec in duration and switches phase at approximately 6 msec. During the first few milliseconds of each phase, the voltage 710 applied to the body of the patient rises asymptotically to an amplitude of about 2000 V (for a 200Ω patient). To achieve the shape of the voltage waveform 710 shown in FIG. 7D, the smoothing capacitor 106 (FIG. 1) may be omitted or set to a value of zero. Such a ramped asymptotic voltage waveform as shown in FIG. 7D may reduce the amount of trauma to the patient's heart during defibrillation, by avoiding the step impulse in voltage shown in each of FIG. 2-6.

Figure 7E:
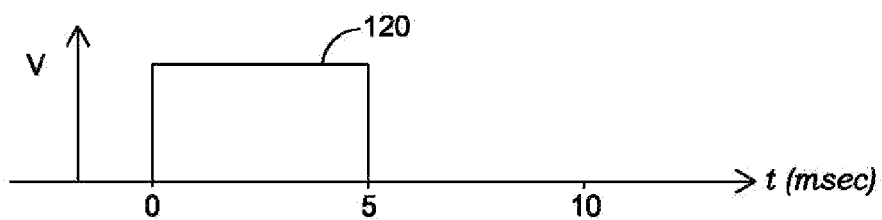
Figure 7F:
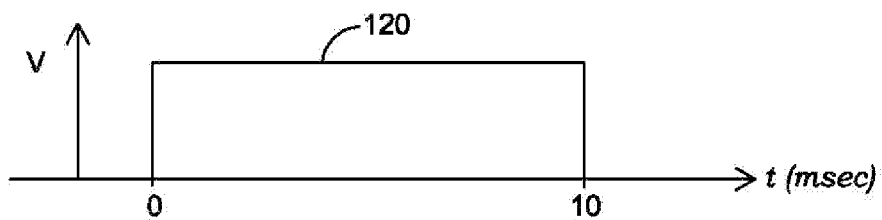

FIGS. 7E and 7F illustrate alternative phase profiles that may be used with the current profile 110 discussed above with respect to FIG. 7A. For example, FIG. 7E illustrates a desired phase profile 120 having two opposing phases over a 10 msec duration, in which the opposing phases are substantially similar in duration (i.e., about 5 msec each). Such a phase profile may be used to balance the amount of charge delivered to the patient's heart in each direction and thereby potentially reduce the trauma to the patient's heart. FIG. 7F illustrates yet an alternative phase profile that may be used to provide a monophasic defibrillating shock to the body of the patient.

It should be appreciated that a variety of different current profiles 110 and phase profiles 120 may be used with the boost converter circuit 100 of FIG. 1 to generate a corresponding variety of different defibrillating waveforms, each having a different shape and/or amplitude and/or phase. For example, the current profile 110 could include a simple exponential waveform or a damped sine wave, and the phase profile 120 could be monophasic, biphasic, triphasic, or otherwise. Accordingly, where it is determined that a particular shape, amplitude, phase, sequence of phases, or all of the above is particularly effective, reference waveforms may be generated and used as desired current profile 110 and desired phase profile 120 to achieve the desired resultant defibrillating waveform. Although not depicted in FIG. 1, each of the desired current profile 110 and the desired phase profile 120 may be stored in a memory, and provided, for example, by a processor of the defibrillator to comparator 118 and each of H-bridge switches 111 to vary the shape, amplitude, or phase of the defibrillating waveform applied to the patient as desired.

Figure 8:
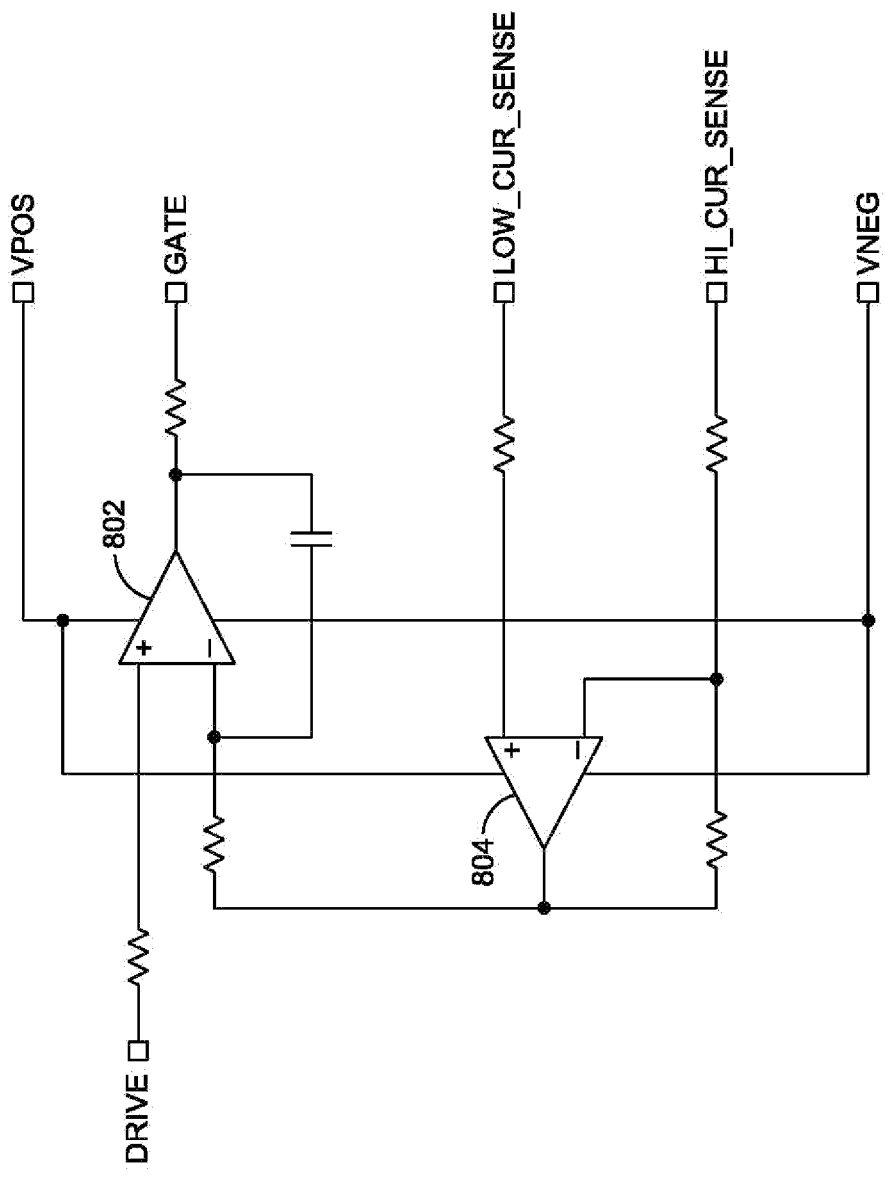
FIG. 8 is a schematic drawing of a drive circuit for switches used in an H-bridge sub-circuit of the circuit of FIG. 1.

Referring back to FIG. 1, again, within each H-bridge switch, 111a-d, is a driver circuit (i.e., 117a, 117b, 117c, and 117d). These circuits are feedback systems illustrated in greater detail in FIG. 8. Each driver circuit is configured to control a switching transistor (i.e., 116a, 116b, 116c, and 116d, respectively) to pass a current up to a controlled maximum level above which the current is clipped.

In each driver circuit is an operational amplifier, 802, connected to receive a control signal, DRIVE, that is based upon the desired phase profile 120 and produce an output, GATE, which turns a switching transistor (FIG. 1, 116a, 116b, 116c, and 116d) on and off as required. A second operational amplifier, 804, is connected to sense current through each switching transistor (FIG. 1, 116a, 116b, 116c, and 116d), and control an input to operational amplifier, 802, so a voltage at output, GATE, turns the switching transistor on up to a desired maximum current through the switching transistor. In the embodiment depicted in FIG. 1, each of the switching transistors 116a, 116b, 116c, and 116d is an IGBT that may be operated in a non-linear mode as a two state (i.e., on or off) switch, or in a linear mode as a voltage controlled current source. Where the circuit 100 is used to provide therapeutically effective amounts of energy sufficient for defibrillation, the switching transistors 116a, 116b, 116c, and 116d would typically be operated in the non-linear mode (e.g., as a two state switch) to avoid thermal destruction. However, by adjusting the timing defined by controller circuit, 107, the desired current profile, 110, and the desired phase profile, 120, the circuit of FIG. 1 can be programmed to perform pacing, as well as defibrillation. For example, by appropriately controlling the timing defined by the controller circuit 107 and the desired current profile 110, and at energies typically used for pacing, the smoothing capacitor 106 can substantially correspond to a DC power supply of a desired voltage. By then providing a suitable phase profile to pairs of H-bridge switches (i.e., 111a and 111c, 111b and 111d), the switching transistors of a respective pair of H-bridge switches may be operated in their linear mode to provide a desired pacing waveform.

Figure 9:
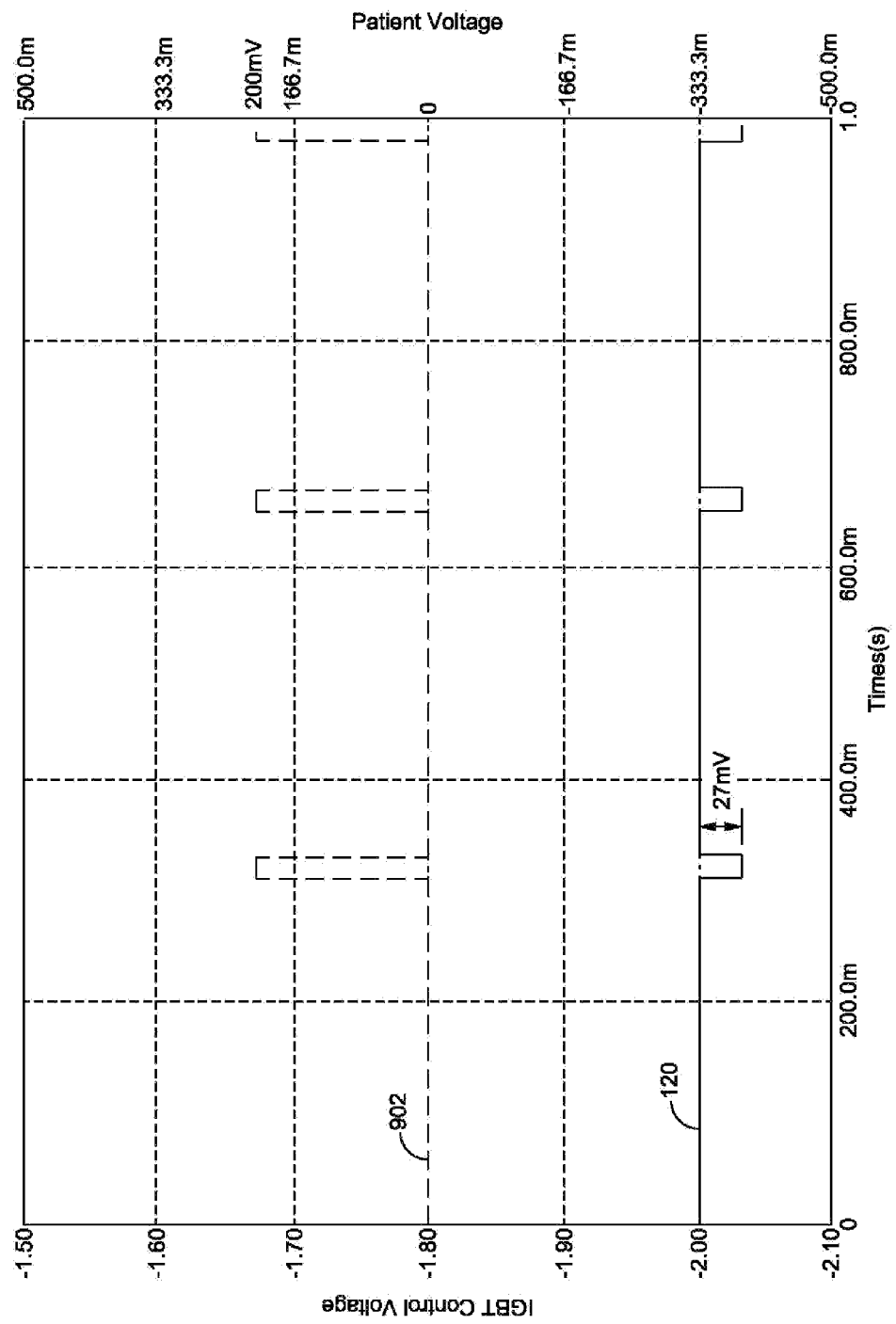
FIG. 9 is a graph of electrical waveforms produced by the circuit of FIG. 1 with a patient load of 25Ω, when programmed for pacer mode.
Figure 10:
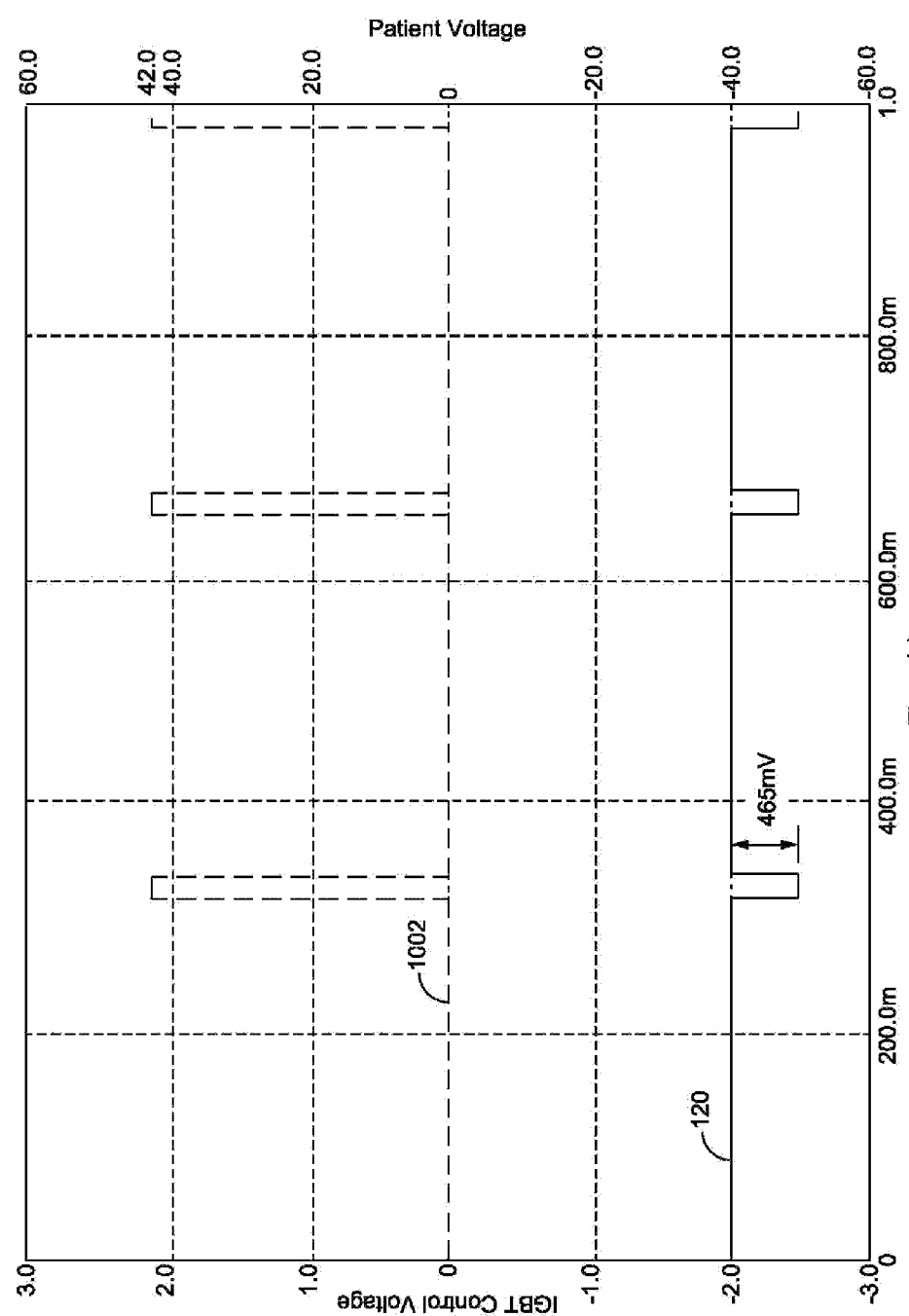
FIG. 10 is a graph of electrical waveforms produced by the circuit of FIG. 1 with a patient load of 300Ω, when programmed for pacer mode.

FIGS. 9 and 10 illustrate a phase profile 120 that may be provided to pairs of H-bridge switches, 111a and 111c or 111b and 111d, to deliver suitable pacing waveforms 902, 1002, to a patient load 102, when the timing defined by the controller circuit 107 and the current profile 110 have been appropriately programmed In each of FIGS. 9 and 10, the timing of the controller circuit 107 and the current profile 110 have been programmed so that smoothing capacitor 106 effectively operates as a 50 V D.C. voltage source. As illustrated in FIG. 9, a voltage level of approximately 27 mV provided to the DRIVE input of driver circuits 117A and 117C is sufficient to deliver an 8 mA, 200 mV pacing pulse into a patient 102 presenting a 25Ω load. As illustrated in FIG. 10, a voltage level of approximately 465 mV is sufficient to deliver an 140 mA, 42 V pacing pulse into a patient 102 presenting a 300Ω load. By appropriately controlling the phase profile 120, pacing pulses ranging from a few milliamps to two hundred milliamps or more may be provided to a patient, using the same circuit topology as that used to deliver a defibrillating shock.

It should be appreciated that although embodiments of the present invention have been primarily described with respect to defibrillation and pacing, they may also be used to deliver other types of therapeutic waveforms to the body of a patient in which the energy delivered is between the ranges of energy typically used for pacing or defibrillation. For example, pacing pulses typically range from a few mA to approximately 200 mA, and defibrillation pulses typically range from about 1 A to about 35-40 A. Between these ranges of current exists a wide spectrum of energies that may be applied to the body of a patient for a variety of therapeutic purposes, for example, to perform charge bumping of a patient's heart, etc. Accordingly, by varying the timing of the controller circuit, the current profile 110, and the phase profile 120, embodiments of the present invention may be used to tailor one or more of the shape, the voltage, and the current of a therapeutic waveform to be applied to the body of a patient.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A system to deliver a therapeutic quantity of energy to a patient load, the system comprising:
   a capacitor having a rated energy storage capacity substantially equal to the therapeutic quantity of energy;
   a boost converter coupled with the capacitor and constructed to release energy from the capacitor at a substantially constant current for a time interval, the boost converter comprising an inductor coupled with the capacitor, a current sensing network, and a solid-state switch coupled between the inductor and the current sensing network; and
   an H-bridge circuit coupled with the boost converter and constructed to apply the substantially constant current in a biphasic voltage waveform to the patient load.

2. The system of claim 1, wherein the boost converter further comprises a controller circuit coupled with the solid state switch and the current sensing network and constructed to cycle the solid state switch.

3. The system of claim 2, wherein the current sensing network is constructed to receive a current profile and compare the current profile with a received current from the solid state switch.

4. The system of claim 1, wherein the H-bridge circuit comprises a plurality of switches, each of the plurality of switches including a circuit constructed to control the switch and to receive a phase profile having a first phase and a second phase.

5. The system of claim 4, wherein the H-bridge circuit further comprises an inverter coupled with at least two of the plurality of switches to invert the phase profile.

6. The system of claim 5, wherein at least two switches of the plurality of switches are configured to be in an open state during the first phase and in a closed state during the second phase.

7. The system of claim 1, wherein the boost converter circuit is further constructed to compensate for voltage droop on the capacitor and variation in the patient load over the time interval.

8. The system of claim 1, wherein the therapeutic quantity of energy and the time interval are selected to defibrillate a patient whose heart is in fibrillation.

9. The system of claim 1, wherein the therapeutic quantity of energy and the time interval are selected to pace a patient whose heart requires pacing impulses.

10. A method of delivering a therapeutic quantity of energy to a patient load, the method comprising:
storing a quantity of energy substantially equal to the therapeutic quantity of energy in a capacitor;
releasing the stored quantity of energy at a relatively constant current during a time interval using a boost converter coupled with the capacitor by transferring energy to an inductor coupled with the capacitor and sensing an amount of current through a solid state switch coupled between the inductor and a current sensing network; and
delivering a first portion of the stored quantity of energy in a first direction to the patient load using an H-bridge circuit coupled with the boost converter.

11. The method of claim 10, wherein the method further comprises delivering a second portion of the stored quantity of energy in a second direction to the patient load using the H-bridge circuit.

12. The method of claim 11, wherein the H-bridge circuit comprises a plurality of switches and wherein delivering a first portion of the stored quantity energy in a first direction and a second portion of the stored quantity of energy in a second direction includes controlling the plurality of switches.

13. The method of claim 12, wherein controlling the plurality of switches includes receiving a phase profile having a first phase and a second phase.

14. The method of claim 13, wherein controlling the plurality of switches further includes changing a state of at least 4 switches of the plurality of switches in response to receiving a change in the phase profile from the first phase to the second phase.

15. The method of claim 10, wherein releasing the stored quantity of energy further includes cycling the solid state switch using a controller circuit coupled with the solid state switch and the current sensing network.

16. The method of claim 15, wherein releasing the stored quantity of energy further includes receiving a current profile and comparing the current profile with the amount of current through the solid state switch using the current sensing network.

17. The method of claim 10, wherein releasing the stored quantity of energy includes compensating for voltage droop on the capacitor and variation in patient load impedance over the time interval.

18. The method of claim 10, wherein the method further comprises determining the therapeutic quantity of energy and the time interval to defibrillate a patient whose heart is in fibrillation.

19. The method of claim 10, wherein the method further comprises determining the therapeutic quantity of energy and the time interval to pace a patient whose heart requires pacing impulses.

20. A system to deliver a therapeutic quantity of energy to a patient load, the system comprising:
a capacitor having a rated energy storage capacity substantially equal to the therapeutic quantity of energy;
a boost converter coupled with the capacitor and constructed to receive a current profile and release energy from the capacitor at a substantially constant current for a time interval consistent with the received current profile; and
an H-bridge circuit coupled with the boost converter and constructed to apply the substantially constant current in a biphasic voltage waveform to the patient load.

* * * * *